United States Patent
Armentrout (10) Patent No.: US 9,237,763 B2
(45) Date of Patent: Jan. 19, 2016

(54) SYNBIOTIC PRODUCT

(75) Inventor: Richard W. Armentrout, Decatur, IL (US)

(73) Assignee: Tate & Lyle Ingredients Americas LLC, Hoffman Estates, IL (US)

(*) Notice: Subject to any disclaimer, the term of this patent is extended or adjusted under 35 U.S.C. 154(b) by 230 days.

(21) Appl. No.: 13/213,663

(22) Filed: Aug. 19, 2011

(65) Prior Publication Data

US 2012/0052152 A1 Mar. 1, 2012

Related U.S. Application Data

(60) Provisional application No. 61/376,888, filed on Aug. 25, 2010.

(51) Int. Cl.
| | | |
|---|---|---|
| A23K 3/00 | (2006.01) | |
| A23F 3/16 | (2006.01) | |
| A23K 1/00 | (2006.01) | |
| A23B 7/10 | (2006.01) | |
| A23F 3/00 | (2006.01) | |
| A23L 1/22 | (2006.01) | |
| A23L 1/20 | (2006.01) | |
| A23L 1/182 | (2006.01) | |
| A01N 63/00 | (2006.01) | |
| A61K 47/00 | (2006.01) | |
| C12P 19/04 | (2006.01) | |
| C12N 1/20 | (2006.01) | |

(Continued)

(52) U.S. Cl.
CPC .............. *A23L 1/3014* (2013.01); *A23K 1/009* (2013.01); *A23K 1/1643* (2013.01); *A23L 1/308* (2013.01); *A61K 35/742* (2013.01)

(58) Field of Classification Search
USPC .............. 426/53, 626, 49, 52, 277, 627; 435/252.5, 101; 424/93.462, 439
See application file for complete search history.

(56) References Cited

U.S. PATENT DOCUMENTS

| 4,110,477 A | 8/1978 | Naruse et al. |
| 6,203,797 B1 | 3/2001 | Perry |

(Continued)

FOREIGN PATENT DOCUMENTS

| CA | 2007270 | 8/1990 |
| CN | 101537020 A | 9/2009 |

(Continued)

OTHER PUBLICATIONS

"Tate & Lyle launches second Promitor (TM) dietary fiber". Available online at http://newhope360.com on Jul. 18, 2007.*

(Continued)

*Primary Examiner* — Rena L Dye
*Assistant Examiner* — Assaf Zilbering
(74) *Attorney, Agent, or Firm* — McDonnell Boehnen Hulbert & Berghoff LLP (57) ABSTRACT

The present invention relates to a synbiotic product composition comprising a blend or mixture of a prebiotic carbohydrate and a probiotic spore-forming *Bacillus* bacteria. Examples of prebiotic carbohydrates useful in synbiotic product include arabinoxylan, arabinoxylan oligosaccharides, xylose, soluble fiber dextrin, soluble corn fiber, and polydextrose. The present invention also relates to human foodstuffs and animal feed comprising such synbiotic products and methods of increasing the titer of spore-forming bacteria in the intestinal tracts of mammals by administration of symbiotic products.

30 Claims, 2 Drawing Sheets (51) Int. Cl.
A23L 1/30 (2006.01)
A23K 1/16 (2006.01)
A23L 1/308 (2006.01)
A61K 35/742 (2015.01)

(56) References Cited

U.S. PATENT DOCUMENTS

| | | | |
|---|---|---|---|
| 6,811,786 | B1 | 11/2004 | Farmer et al. |
| 6,849,256 | B1 | 2/2005 | Farmer |
| 6,905,692 | B2* | 6/2005 | Farmer ..................... 424/260.1 |
| 6,942,754 | B2 | 9/2005 | Izumi et al. |
| 2003/0077255 | A1 | 4/2003 | Sabharwal |
| 2005/0079244 | A1 | 4/2005 | Giffard et al. |
| 2005/0271643 | A1* | 12/2005 | Sorokulova et al. ..... 424/93.462 |
| 2008/0102162 | A1 | 5/2008 | Delcour et al. |
| 2008/0199444 | A1 | 8/2008 | Cui et al. |
| 2008/0292766 | A1 | 11/2008 | Hoffman et al. |

FOREIGN PATENT DOCUMENTS

| | | |
|---|---|---|
| CN | 101744239 | 6/2010 |
| WO | 2004052121 | 6/2004 |
| WO | 2007050656 | 5/2007 |
| WO | 2009/026306 A2 | 2/2009 |
| WO | 2010/015580 A1 | 2/2010 |

OTHER PUBLICATIONS

Numan et al., "Dietary Fiber Content and Composition in Six Cereals at Different Extraction Rates". Cereal Chemistry 61(1):14-19.*

Bosscher D., "Chapter 6: Fructan Prebiotics Derived from Inulin". Prebiotics and Probiotics Science and Technology, vol. 1, pp. 169-170. Jun. 2009.*

Palframan et al., "Development of a quantitative tool for the comparison of the prebiotic effect of dietary oligosaccharides." Letters in Applied Microbiology 2003, 37, 281-284.*

Casula et al., "Bacillus Probiotics: Spore Germination in the Gastrointestinal Tract", Applied and Environmental Microbiology, May 2002, pp. 2344-2352, vol. 68.

De Vecchi et al., "Lactobacillus Sporogenes or Bacillus Coagulans: Misidentification or Mislabelling?", International Journal of Probiotics and Prebiotics, 2006, pp. 3-10, vol. 1 No. 1.

Duc et al, "Characterization of Bacillus Probiotics Available for Human Use", Applied and Environmental Microbiology, Apr. 2004, pp. 2161-2171, vol. 70, No. 4.

Gibson, Glenn R., "Dietary Modulation of the Human Gut Microflora Using the Prebiotics Oligofructose and Inulin", The Journal of Nutrition, 1999, pp. 1438S-1441S, vol. 129.

Green et al, "Characterization of Two Bacillus Probiotics", Applied and Environmental Microbiology, Sep. 1999, pp. 4288-4291, vol. 65 No. 9.

Leser et al, "Germination and Outgrowth of Bacillus Subtilis and Bacillus Licheniformis Spores in the Gastrointestinal Tract of Pigs", Journal of Applied Microbiology, 2007, pp. 1025-1033, vol. 104.

Marseglia et al, "Efficacy of Bacillus clausii spores in the prevention of recurrent respiratory infections in children: a pilot study", Therapeutics and Clinical Risk Management, 2007, pp. 13-17, vol. 3 No. 1.

Roberfroid et al., "The Bifidogenic Nature of Chicory Inulin and Its Hydrolysis Products", The Journal of Nutrition, 1998, pp. 11-19, vol. 128.

Tuohy et al., "A Human Volunteer Study to Determine the Prebiotic Effects of Lactulose Powder on Human Colonic Microbiota", Microbial Ecology in Health and Disease, 2002, pp. 165-173, vol. 14.

Fujiya et al, "The Bacillus subtilis Quorum-Sensing Molecule CSF Contributes to Intestinal Homeostasis via OCTN2, a Host Cell Membrane Transporter", Cell Host & Microbe, 2007, pp. 299-308.

Guo et al., "Screening of Bacillus strains as potential probiotics and subsequent confirmation of the in vivo effectiveness of Bacillus subtilis MA139 in pigs", Antonie van Leeuwenhoek, 2006, pp. 139-146, vol. 90.

Canani et al., "Probiotics for treatment of acute diarrhoea in children: randomised clinical trial of five different preparations", British Medical Journal, 2007, pp. 340-342, vol. 335.

Urdaci et al., "Bacillus clausii Probiotic Strains: Antimicrobial and Immunomodulatory Activities", Journal of Clinical Gastroenterology, Jul. 2004, pp. S86-S90, vol. 38, Supp. 2.

Jahoor et al., "Peroxisome Proliferator-Activated Receptors Mediate Host Cell Proinflammatory Responses to Pseudomonas aeruginosa Autoinducer", Journal of Bacteriology, Jul. 2008, pp. 4408-4415, vol. 190, No. 13.

Spinosa et al., "On the fate of ingested Bacillus spores", Research in Microbiology, 2000, pp. 361-368, vol. 151.

Gibson, Glenn R., "Dietary modulation of the human gut microflora using prebiotics", British Journal of Nutrition, 1998, 5209-5212, vol. 80, Suppl. 2.

La Rosa et al., "Prevention of Antibiotic-Associated Diarrhea with Lactobacillus Sporogens and Fructo-Oligosaccharides in Children. A Multicentric Double-Blind VS Placebo Study", Minerva Pediatrica, 2003, pp. 447-452, vol. 55, No. 5.

Mazza, Piergiorgio, "The use of Bacillus subtilis as an antidiarrhoeal microorganism", Bollettino chimico farmacutico, 1994, pp. 3-18, vol. 133, No. 1.

Shibanuma et al, "Patrial Acid Hydrolysis of Corn Fiber for the Production of L-Arabinose", Journal of Applied Glycoscience, 1999, pp. 249-256, vol. 46, No. 3.

Hartemink, R., "Bacillus coagulans (Lactobacillus sporogenes) a probiotic?", Food-Info, 2007, obtained online at www.food-info.net/uk/ff/sporogenes.htm.

FAO Technical Meeting on Prebiotics, Food Quality and Standards Service, Food and Agriculture Organization of the United Nations, Sep. 2007.

Sugawa-Katayama et al., "Effects of Pullulan, Polydextrose and Pectin on Cecal Microflora", Oyo Toshitsu Kagaku, 1994, pp. 413-418, vol. 41 No. 4.

R. Palframan et al., "Development of a quantitative tool for the comparison of the prebiotic effect of dietary oligosaccharides," Letts. in Applied Microbiol., 37, 281-84 (2003).

Slavin et al., "Partially hydrolysed guar gum: clinical nutrition uses," Nutrition, 19, 549-552, (2003).

Giannini et al., "Role of partially hydrolyzed guar gum in the treatment of irritable bowel syndrome," Nutrition, 22, 334-342 (2006).

Maathuis et al., "The Effect of the Undigested Fraction of Maize Products on the Activity and Composition of the Microbiota Determined in a Dynamic in Vitro Model of the Human Proximal Large Intestine," J. Am. Coll. Nutrition, 28, 657-66 (2009).

Yajun Du, "Study on Proliferation of Water-Soluble Dietary Fibers on Intestinal Probiotics," Food Sci. and Tech. (China), vol. 10, 130-33.

* cited by examiner

* The SEM for "None" (no added carbohydrates) is indicated (four independent experiments).

SYNBIOTIC PRODUCT

CROSS REFERENCE TO RELATED APPLICATIONS

This application claims the benefit of U.S. Provisional Patent Application No. 61/376,888, filed Aug. 25, 2010, which is incorporated herein by reference in its entirety.

STATEMENT REGARDING FEDERALLY SPONSORED RESEARCH OR DEVELOPMENT

Not Applicable.

BACKGROUND

The present invention relates to novel synbiotic products comprising a combination of spore-forming probiotic bacteria with prebiotic compounds capable of providing nutrients to the probiotic bacteria and/or capable of encouraging the growth of resident beneficial bacteria, such as *Lactobacillus* or *Bifidobacterium*, present in the gastro-intestinal tract. Such synbiotic product compositions may enhance the health benefits of food products containing such synbiotic compositions.

There is increasing demand for functional food ingredients, both for human and animal consumption, that deliver health benefits in addition to nutrition. One class of such health-related food ingredients are known as "prebiotic" compounds. Representative examples of prebiotic compounds that are currently used in food products include a wide variety of carbohydrates, such as various sugars and starches. Many carbohydrates that have caloric value are digested to monosaccharides or short-chain oligosaccharides in the human upper gastro-intestinal tract (e.g., the mouth, the stomach, and the small intestine) and are readily absorbed into the blood stream. In addition to such readily metabolized carbohydrates, some carbohydrates act as dietary "fiber" in food products. Fiber compounds are generally not broken down, or only partially digested, in the upper gastro-intestinal tract and substantial amounts pass into the colon relatively intact. The benefits of fiber to human health are well established and recognized by nutrition scientists worldwide, such as, for example, in US government dietary recommendations. Studies have suggested that diets rich in dietary fiber can reduce the risk of cardiovascular disease, cancer, gastrointestinal problems, and obesity. See Campos et al., Nutr Hosp. 2005 January-February; 20(1):18-25 (suggesting a link between the occurrence of colorectal cancer and low fiber diet); Kendall et al., Curr Atheroscler Rep. 2004 November; 6(6):492-8 (suggesting that a diet rich in fiber can reduce LDL cholesterol); Kendall et al., J AOAC Int. 2004 May-June; 87(3):769-74 (suggesting that a diet high in fiber can reduce the risk of chronic disease); Cernea et al., Acta Diabetol. 2003 40 suppl 2:S389-400 (suggesting that a diet high in fiber can reduce the risk of cardiovascular disease).

There is increasing evidence that many of the health-promoting effects of dietary fiber are due to fermentation of these carbohydrates by a complex consortia of microorganisms (the microbiota) in the large intestine (Gibson, Glenn, "Dietary modulation of the human gut microflora using prebiotics," Journal Of Nutrition, 80(2):S209-S212 (1998)). A sub-class of carbohydrate fibers, "prebiotic" carbohydrate compounds, have been reported to be especially beneficial in promoting and maintaining health in normal humans. Representative examples of dietary fiber carbohydrates with established prebiotic activity are inulin and fructo-oligosaccharides (Roberfroid, et al., "The Bifidogenic Nature of Chicory Inulin and Its Hydrolysis Products," Journal of Nutrition, 128, 1, 11-19, 1998. Gibson, "Dietary Modulation of the Human Gut Microflora Using the Prebiotics Oligofructose and Inulin," Journal of Nutrition, 129, 7 Suppl., 1438S-1441S, 1999); lactulose (Tuohy, et al., "A human volunteer study to determine the prebiotic effect of lactulose on human colonic microbiota," Micro. Ecol. Health Disease 14, 165-173 (2002)); and soluble corn fiber (SCF) (U.S. patent application Ser. No. 12/124,364).

In addition to "prebiotic" ingredients, there is a growing market for foodstuffs and animal feeds that are formulated with "probiotic" bacteria. For example, there is increasing interest in the use of probiotic organisms as feed additives for animals, primarily as possible replacements for antibiotics. Many bacteria that are considered to have beneficial probiotic properties are normal commensal bacteria present in the healthy human or animal gut microflora. The most frequently used human probiotics include the *Lactobacilli* and *Bifidobacteria*. However, use of either of these bacterial groups as probiotic food or feed additives is fraught with difficulties. In order to be of benefit, the bacteria must survive the manufacturing process as viable cells, and be formulated as stable products (i.e., no significant loss of viability on storage for long periods and sometimes under adverse conditions). In addition, the bacteria must survive passage through the extreme acidity of the stomach and exposure to bile salts in the upper small intestine. It is hypothesized that the beneficial effects of probiotics are due to brief colonization of the small intestine and/or the colon which entails successfully competing with the existing microbiota that number some $10^7$ to $10^{11}$ living bacteria per gram of luminal contents.

Several types of spore-forming *Bacillus* are currently sold as probiotics for both human and animal applications. For example, it has been reported that *B. subtilis* is sold over-the-counter for a variety of intestinal problems (Casula and Cutting (2002), Applied Environmental Microbiology, May 2002, pp. 2344-2352; Green, DH, et al. (1999) Appl. Env. Microbiol. 65, pp. 4288-4291) and for the treatment of diarrhea (Mazza, P (1994) Boll. Chim. Farm. 133, pp. 3-18). Studies of commercial preparations of *B. clausii* have also been reported, for example, by Marseglia, et al. (2007), and Canani, et al. (2007). Marseglia, GL, et al. (1997) Ther. Clin. Risk Manag. 3, pp. 13-17; Canani, RB, et al. (2007) BMJ, August 18, 335(7615): 340.

One of the probiotic strains with the longest history of human use is *Bacillus coagulans*, which was first described in the 1930's as *Lactobacillus sporogenes* ((Devechihi, E. and Drago, L. (2006) Int. J. Probiotics Prebiotics 1, pp. 3-10)). This strain(s) is of particular interest as it is one of the few studied spore-forming strains that produce large amounts of lactic acid from sugars without the production of gas. *B. coagulans* probiotic strains are reported to produce terminal spores and the vegetative cells are facultative anaerobes and motile (Devechihi and Drago, 2006).

Duc et al. evaluated five commercial products that consisted of strains of *Bacillus* spores. Three strains of *B. cereus* were shown to persist in the gastro-intestinal tracts of mice for 18 days, which was taken as evidence of colonization (Duc, L H, et al. (2004) Appl. Environ. Microbiol. 70, pp. 2161-2171). Leser et al. describe the feeding of *B. subtilis* and *B. licheniforms* spores to pigs (Leser, TD, et al. (2008) *J. Appl. Microbiol.* 104, pp. 1025-1033). Within two weeks of the start of feeding these probiotics, spores were found in all regions of the pig gastrointestinal tract. It was estimated that 70-90% of the spores germinated and there was limited and transient vegetative growth in the gastro-intestinal tract.

SUMMARY OF THE INVENTION

The present invention relates to certain symbiotic products comprising at least one prebiotic carbohydrate and at least one probiotic spore-forming Bacillus bacteria. The present invention can also be described as a symbiotic product comprising a prebiotic carbohydrate component comprising a prebiotic carbohydrate and a probiotic spore component comprising a probiotic spore-forming *Bacillus* bacteria. Representative examples of suitable prebiotic carbohydrates include arabinoxylan, arabinoxylan oligosaccharides, xylose, soluble fiber dextrin, soluble corn fiber, and polydextrose. In certain embodiments of the synbiotic product, the prebiotic carbohydrate is arabinoxylan, arabinoxylan oligosaccharides, xylose, soluble fiber dextrin, soluble corn fiber, polydextrose, or mixtures of these carbohydrates. Representative examples of suitable spore-forming *Bacillus* bacteria include *B. subtilis, B. coagulans, B. licheniformis, B. clausii*, and *B. pumilis*. In certain embodiments of the synbiotic product, the spore-forming Bacillus bacteria is *B. subtilis, B. coagulans, B. licheniformis, B. clausii, B. pumilis*, or mixtures of these bacteria.

The synbiotic product of the invention can be used as an ingredient or component in food products. In certain embodiments, a food product comprises the synbiotic product of the invention.

The present invention also relates to a method of increasing the titer of spore-forming *Bacillus* bacteria in the intestinal tract of a mammal by administering the synbiotic product. It is believed that administration of the synbiotic product may provide certain health benefits. In certain embodiments, the synbiotic product is administered by consuming a food product comprising the synbiotic product. In certain embodiments, the mammal is a human and in certain embodiments, the mammal is a non-human mammal.

BRIEF DESCRIPTION OF THE DRAWINGS

FIG. 2.

DETAILED DESCRIPTION

I. DEFINITIONS

As used herein, a "prebiotic" compound is defined as: ". . . a non-viable food component that confers a health benefit on the host associated with modulation of the microbiota" (FAO technical meeting on prebiotics, Sep. 15-16, 2007. Paragraph 3.1. Food Quality and Standards Service (AGNS), Food and Agriculture Organization of the United Nations (FAO)).

As used herein, a "probiotic" bacterium is a: " . . . viable microbial food (or feed) supplement that beneficially influences the health of humans (or animals)." (International Life Science Institute Europe, Functional Food Science in Europe project, (FUFOSE), working group on functional foods).

As used herein unless otherwise specified, a "food product" refers to an edible product, including a beverage, meant for human or animal consumption. Where specified, a "foodstuff" is meant for human consumption and a "feed" is meant for animal consumption.

A "synbiotic product" is a composition comprising a combination of prebiotic and probiotic components.

Synbiotic compositions are effective within certain ranges of administration ("effective amounts") of the carbohydrate components (grams/day) and viable bacterial titers of the probiotic bacteria (CFU/day). The titer of viable bacteria in a product can be expressed as CFU/Gram carbohydrate dosage.

II. OVERVIEW

Novel synbiotic product compositions comprising combinations of probiotic spore-forming bacteria and prebiotic compounds are provided herein that may enhance the health benefits of food ingredients, foodstuffs, feed additives, animal feed, etc., containing such synbiotic compositions. Synbiotic products of the invention enhance the germination, growth, and activity of probiotics, thus increasing the titer of spore-forming probiotic bacteria in the intestinal tract of a host. Without being bound by theory, the synbiotic product compositions are believed to provide improved benefits in human and animal health, well-being, and productivity, specifically through reduced stress due to lower morbidity, improved immune status, improved feed conversion efficiency, and enhanced ease of formulation of foodstuffs/feeds, foodstuffs/feed handling and storage, and flexibility of foodstuffs/feed delivery. The compositions may also be effective at smaller dosages in comparison to presently known probiotic products.

III. PREBIOTIC CARBOHYDRATE

In addition to prebiotic carbohydrates such as inulin, fructo-oligosaccharides, lactulose, and soluble corn fiber (SCF), there is evidence that a number of additional compounds that undergo limited digestion or absorption in the upper gastro-intestinal tract can passage to the lower gastro-intestinal tract and undergo fermentation by the resident microbiota.

Without being bound by theory, it is thought that the benefits of spore-forming *Bacillus* strains come from spores surviving passage through the manufacturing process and through the stomach and that they germinate in the intestines, where they are active and beneficial. These strains of *Bacillus* grow vegetatively on glucose and amino acids in vitro, but in vivo are required to compete in the upper gastro-intestinal tract with the host animal's need for these nutrients. Currently used probiotic spore powders are packaged with maltodextrin, which is no better than glucose as a potential food source for germinating spores in the upper intestine as host animals also rapidly digest and absorb maltodextrin.

In contrast, it has been found that certain plant-derived carbohydrate compounds such as arabinoxylan ("AX") (a form of plant hemicellulose, especially that derived from corn and corn fiber), arabinoxylan oligosaccharides ("AXOS") (a processed form of AX in which the high molecular weight polymer is cleaved to smaller fragments), and xylose ("X") (one of the monosaccharide substituents of AX and AXOS that is released by acid or enzymatic hydrolysis of these polymers) may be especially suitable as prebiotic carbohydrates for use in a synbiotic product composition in conjunction with spore-forming *Bacillus* strains (Examples 1 and 2).

In certain embodiments of the present invention, a prebiotic carbohydrate is selected from the group consisting of arabinoxylan, arabinoxylan oligosaccharides, xylose, and mixtures thereof. Other prebiotic carbohydrates useful in the invention include soluble fiber dextrin (SFD), soluble corn fiber (SCF), and/or polydextrose (PDX). In certain embodiments, a prebiotic carbohydrate compound is selected from the group consisting of arabinoxylan, arabinoxylan oligosaccharides, xylose, soluble fiber dextrin, soluble corn fiber, polydextrose, and mixtures thereof. One of skill in the art will also appreciate that there are numerous other prebiotic carbohydrates that may be suitable for use in combination with arabinoxylan, arabinoxylan oligosaccharides, xylose, soluble fiber dextrin, soluble corn fiber, and polydextrose, representative examples of which include inulin, fructo-oligosaccharide, lactulose, glucose, and maltodextrin.

A. Arabinoxylan (AX)

AX is the hemicellulose that can be solubilized from corn fiber by aqueous extraction.

B. Xylose (X)

Xylose is the monosaccharide that makes up the xylan polymer backbone of the corn fiber hemicellulose polymer, arabinoxylan. It is produced by acid or enzymatic hydrolysis of hemicellulose. Xylose is a highly soluble, crystalline, dry powder. It is an abundant, relatively inexpensive, sweet-tasting, natural compound that is sold in some countries as a low calorie sweetener.

C. Arabinoxylan Oligosaccharides (AXOS)

AX is the hemicellose that can be solubilized from corn fiber by aqueous extraction. AX is a collection of high molecular weight polymers than can be converted to oligosaccharides (AXOS) by, for example, digestion with endoxylanases. Based upon the limited, but positive growth of at least four known probiotic Bacillus on high molecular weight AX, and the strong growth of at least two of the four same strains on xylose, it is believed that AXOS will also be metabolized by these and other probiotic Bacillus strains.

Methods for obtaining arabinoxylan, xylose, and arabinoxylan oligosaccharides are known to those of skill in the art. For example, xylose and/or arabinoxylan oligosaccharides can be obtained by chemical and/or enzymatic processing of hemicellulose from wood and other plant materials. These lignocellulosic substrates comprise cellulose, hemicellulose, and lignin. These types of substrates may be made accessible for hydrolysis by steam and/or mild acid or alkali treatment. Since hemicellulose is generally easier to hydrolyze to sugars than cellulose, it is preferable to first prehydrolyze the hemicellulose material and separate the soluble pentose sugars and soluble arabinoxylan oligosaccharides from the insoluble cellulose-containing residue. Hydrolysis may be done using enzymes (hemicellulase(s)), for example, or chemical treatments (e.g., by acid treatment) or a combination of the two.

For example, as described in U.S. Pat. No. 6,942,754, xylooligosaccharides are produced from a lignocellulose pulp by enzyme treating with hemicellulase, filtering the resultant reaction mixture to separate a liquid fraction from the enzyme-treated pulp, subjecting the separated liquid fraction to a permeation treatment through a separation membrane to separate a non-permeated fraction containing xylooligosaccharide-lignin complex with an increased concentration from a permeated fraction, collecting the non-permeated fraction, and separating and recovering xylooligosaccharide from the collected non-permeated fraction.

For example, monosaccharides xylose and arabinose of the hemicellulose of monocotyledonous plants can be obtained by mild acid hydrolysis of plant material as described in Shibanuma, K., et al. (1999) J. Appl. Glycosci. 46, 249-56. The resulting soluble fraction of the hydrolysate can be fractionated, using methods described above, to give the monosaccharides and a mixture of arabinoxylan oligomers.

IV. PROBIOTIC BACTERIA

Probiotics are living microbes that have beneficial effects on humans and/or animals when ingested. Currently in human foods, probiotics are most often species of either Lactobacillus or Bifidobacterium. Neither of these types of bacteria forms spores. It has been reported, however, that certain microorganisms with probiotic properties include bacteria capable of forming heat-resistant and extremely stable spores. Representative examples of such spore-forming bacteria include various spore-forming Bacillus species including, but not limited to, B. subtilis, B. coagulans, B. licheniformis, B. pumilis, and B. clausii. The spores, in many cases, survive exposure to heat exceeding 100° C. This heat resistance allows the spores to survive even extreme manufacturing processes. In general, spores can be produced in good yield in industrial-scale pure-culture fermentations. Spores tend to be much more heat and oxygen resistant than vegetative bacteria and thus survive processing conditions better than bacteria that do not form spores. In dry, powdered form, spores can survive for decades. In general, there is only a slight loss of viability in the dry spore commercial products over a two year period in a sealed package. It has been reported that Bacillus spores can survive passage through the stomach, are resistant to bile salt exposure, and germinate in the ileum. Casula, G, and Cutting, SM (2002) Applied Environmental Microbiology, May 2002, pp. 2344-2352.

Many Bacillus strains grow well and form spores efficiently on inexpensive minimal media under well-understood aerobic fermentation conditions using existing equipment without special modification. In certain embodiments of the present invention, the bacterium is a spore-forming Bacillus species with probiotic effects. In certain embodiments, the probiotic spore-forming Bacillus is selected from the group consisting of B. subtilis, B. coagulans, B. clausii, B. licheniformis, B. pumilis, and mixtures thereof.

The spore-forming probiotic Bacillus species of the invention do not require any special methods of production such as manufacture, handling, packaging and the like that go beyond what is well known to one of skill in the art. Methods for production of the probiotic spores use fermentation and recovery methods well known in the art. For example, the respective bacterial species are seeded from standard stock into a reactor and grown in standardized media until a predetermined CFU/gram concentration is reached and sporulation has occurred. The bulk material is then drained from the reactor and dried by one of a variety of standard methods, such as spray drying. Other representative examples of such art known methods include submerged fermentation, recovery & concentration by filtration, and packaging in moisture-proof systems.

V. SYNBIOTIC PRODUCTS

The synbiotic products of the present invention are novel combinations of probiotic live spore-forming bacteria and prebiotic compounds that are believed to achieve a synergistic effect. In certain embodiments of the present invention, a symbiotic product is a combination of at least one probiotic spore-forming Bacillus bacteria and at least one prebiotic carbohydrate. Such synbiotic products can be used as ingredients in foodstuffs and animal feed. In certain embodiments, the synbiotic product comprises at least one probiotic spore-forming Bacillus bacteria selected from the group consisting of B. subtilis, B. coagulans, B. licheniformis, B. clausii, B. pumilis, and mixtures thereof. In certain embodiments, the synbiotic product comprises at least one prebiotic carbohydrate selected from the group consisting of arabinoxylan ("AX"), arabinoxylan oligosaccharides ("AXOS"), xylose ("X"), soluble fiber dextrin ("SFD"), soluble corn fiber ("SCF"), polydextrose ("PDX"), and mixtures thereof. It is also contemplated that in certain embodiments, the synbiotic product also comprises inulin, fructo-oligosaccharide, lactulose, glucose, and maltodextrin. One of skill in the art will recognize that there are numerous embodiments encompassing different combinations of at least one probiotic spore-forming *Bacillus* bacteria and at least one prebiotic carbohydrate, all of which are contemplated herein.

In certain embodiments, the synbiotic product composition of spore-forming *Bacillus* bacteria and prebiotic carbohydrate is a dry powder. In certain embodiments the dry powder is a flowable powder, as measured by ASTM Standard D6128-97 (1998) American Soc. for testing and materials: "Standard shear-testing method for bulk solids using the Jenike shear cell." In certain embodiments, the synbiotic product has less than about 10% moisture content. In certain embodiments, the synbiotic product has less than about 9% moisture content. In certain embodiments, the synbiotic product has less than about 8% moisture content. In certain embodiments, the synbiotic product has less than about 7% moisture content. In certain embodiments, the symbiotic product has less than about 6% moisture content. In certain embodiments, the synbiotic product has less than about 5% moisture content. In certain embodiments, the synbiotic product has from about 1% to about 10% moisture content. In certain embodiments, the synbiotic product has from about 5% to about 10% moisture content. As used herein, moisture content is measured by ASTM standard D6869 American Society for testing and materials: "Karl Fisher" titration.

The synbiotic product of the invention that is a combination of at least one probiotic spore-forming *Bacillus* bacteria and at least one prebiotic carbohydrate can also be described as comprising a prebiotic carbohydrate component and a probiotic spore component wherein the prebiotic carbohydrate component comprises at least one prebiotic carbohydrate and the probiotic spore component comprises at least one probiotic spore-forming *Bacillus* bacteria.

The synbiotic product composition can be prepared by blending an amount of a dry spore component with an amount of a dry prebiotic component. Alternatively, liquid forms of prebiotic components can be mixed with liquid forms of probiotic spore components and the mixture can be dried, such as by spray drying. One of skill in the art will recognize other alternative methods common to commercial manufacture are practical and useful.

Additional ingredients, such as, but not limited to, inert fillers, dispersing materials, preservatives, colorants, and nutrients as are appropriate and known to the industry for food and feed products may be added to achieve desired product characteristics and the desired final range of living spores in the final product.

In certain embodiments, the probiotic spore component of the synbiotic product will contain up to about $10^{11}$ viable spores per gram dry weight. In certain embodiments, the probiotic spore component will contain more than about $10^9$ viable spores per gram dry weight. In certain embodiments, the probiotic spore component will contain from about $10^9$ to about $10^{11}$ viable spores per gram dry weight. In certain embodiments, the probiotic spore component will contain from about $10^9$ to about $10^{10}$ viable spores per gram dry weight. In certain embodiments, the probiotic spore component will contain from about $10^{10}$ to about $10^{11}$ viable spores per gram dry weight. As used herein, viable spores are counted using the commonly used "pour plate" method, an illustrative example of which is described in Example 3.

In certain embodiments, the final synbiotic product composition will comprise more than about $10^5$ viable probiotic spores per gram dry product weight. In certain embodiments, the final symbiotic product composition will comprise up to about $10^7$ viable probiotic spores per gram dry product weight. In certain embodiments, the final synbiotic product composition will contain from about $10^5$ to about $10^7$ viable probiotic spores per gram dry product weight. In certain embodiments, the final synbiotic product composition will contain from about $10^5$ to about $10^6$ viable probiotic spores per gram dry product weight. In certain embodiments, the final synbiotic product composition will contain from about $10^6$ to about $10^7$ viable probiotic spores per gram dry product weight.

For purposes of illustration, a probiotic spore component with a viable titer of $10^9$ probiotic spores per gram dry weight is blended with other dry ingredients to achieve a final titer of, for example, $10^7$ viable spores per gram dry product weight by blending 1 gram of the dry spore component with 100 grams of other dry ingredients including the prebiotic carbohydrate.

VI. FOOD PRODUCTS

The synbiotic products of the invention may be used as an ingredient or component of food products such as human foodstuffs or animal feed. Such food products contain an amount of the synbiotic product such that the food products can be consumed in amount that provides an effective amount of the synbiotic product. Incorporation of ingredients into food products is known in the art and will vary according to the type of food product prepared. Although there are certain food products that have been traditionally marketed as containing prebiotics or probiotics, the types of food products contemplated herein are not limited to a particular type of food product. Representative, non-limiting examples of certain embodiments of food products containing the synbiotic product include supplements, nutritional bars, eternal clinical nutrition preparations, baby food, and coatings for dry foodstuffs, such as coating bakery goods or chewing gum. Prophetic examples of such foodstuffs are provided in the Examples.

VII. METHOD OF INCREASING THE TITER OF SPORE-FORMING *BACILLUS* BACTERIA

Certain embodiments of the invention are directed to methods of increasing the titer of spore-forming *Bacillus* bacteria in the intestinal tracts of a mammal. It is believed that administration of an effective amount of the synbiotic product may provide certain health benefits to humans and non-human mammals such that their health is improved.

In general, it is believed that consumption of probiotics is helpful in the maintenance and regulation of the gastrointestinal tract in normal, healthy individuals. Consumption of probiotics may also help alleviate certain ailments of the gastrointestinal tract, for example, diarrhea. Controlled trials have suggested that probiotics can shorten the course of infectious diarrhea in infants and children. Consumption of probiotics may also help people with Crohn's disease and irritable bowel syndrome. Some studies suggest that certain probiotics may help maintain remission of ulcerative colitis and prevent relapse of Crohn's disease and the recurrence of pouchitis (a complication of surgery to treat ulcerative colitis). Probiotics may also be of use in maintaining urogenital health. Like the intestinal tract, the vagina is a finely balanced ecosystem. The system, however, can be thrown out of balance by a number of factors, including antibiotics, spermicides, and birth control pills. Probiotic treatment that restores the balance of microflora may be helpful for such common female urogenital problems as bacterial vaginosis, yeast infection, and urinary tract infection. It is contemplated that oral and vaginal administration of probiotics may help in the treatment of bacterial vaginosis and urinary tract infection. Consumption of probiotics by animals may provide similar benefits and may be especially beneficial as a cost effective and "natural" alternative to treating animals with antibiotics.

Representative examples of non-human mammals include animals generally considered as livestock such as, but not limited to: horses, cattle, swine, sheep, goats, oxen, llamas, alpacas, and bison. Representative examples of non-human mammals also include rodents such as, but not limited to: mice, rats, rabbits, hamsters, gerbils, and guinea pigs. Representative examples of non-human mammals also include mammalian companion animals such as, but not limited to: cats and dogs. Antibiotics are routinely administered to mammals such as livestock to improve their health. In certain embodiments, administration of the synbiotic product of the invention may provide health benefits to non-human mammals in the absence of administering antibiotics to such mammals.

In certain embodiments, the symbiotic product is administered in an effective amount that increases the titer of spore-forming *Bacillus* bacteria in the intestinal tract containing a sufficient amount of the prebiotic carbohydrate and probiotic bacteria component to provide prebiotic and/or probiotic activity with the limitation that the amount not greatly exceed the tolerance limitations due to the osmotic effects of non-digestible carbohydrates. For humans, dosages of more than about 20 g/day of prebiotic carbohydrate can have unpleasant effects. For animals, one of skill in the art will recognize that amount of synbiotic product administered is adjusted, such as proportional to body weight, to achieve an effective amount of prebiotic carbohydrate and/or probiotic bacteria.

The synbiotic product may be administered infrequently, such as only one day a week, or month, or every several months, or year, etc. The synbiotic product may be administered more frequently, such as from 2 to 6 days a week, or with similar frequency over longer periods of time. The synbiotic product may be administered daily, meaning on consecutive days over at least five days time.

In certain embodiments, the synbiotic product is administered such that the amount of prebiotic carbohydrate is from about 1 g to about 25 g carbohydrate in any single day. In certain embodiments, the synbiotic product is administered daily in such amounts. In certain embodiments, the synbiotic product is administered such that the amount of prebiotic carbohydrate is from about 1 g to about 10 g carbohydrate in any single day. In certain embodiments, the synbiotic product is administered daily in such amounts. In certain embodiments, the synbiotic product is administered such that the amount of prebiotic carbohydrate is from about 1 g to about 20 g carbohydrate in any single day. In certain embodiments, the synbiotic product is administered daily in such amounts. In certain embodiments, the synbiotic product is administered such that the amount of prebiotic carbohydrate is from about 2.5 g to about 10 g carbohydrate in any single day. In certain embodiments, the synbiotic product is administered daily in such amounts. In certain embodiments, the synbiotic product is administered such that the amount of prebiotic carbohydrate is from about 2.5 g to about 20 g carbohydrate in any single day. In certain embodiments, the synbiotic product is administered daily in such amounts. In certain embodiments, the synbiotic product is administered such that the amount of prebiotic carbohydrate is from about 5 g to about 10 g carbohydrate in any single day. In certain embodiments, the synbiotic product is administered daily in such amounts.

In certain embodiments, the synbiotic product is administered such that the amount of prebiotic carbohydrate is from about 5 g to about 20 g carbohydrate in any single day. In certain embodiments, the synbiotic product is administered daily in such amounts. In certain embodiments, the synbiotic product is administered such that the amount of prebiotic carbohydrate is from about 2.5 g to about 25 g carbohydrate in any single day. In certain embodiments, the synbiotic product is administered daily in such amounts. In certain embodiments, the synbiotic product is administered such that the amount of prebiotic carbohydrate is from about 5 g to about 25 g carbohydrate in any single day. In certain embodiments, the synbiotic product is administered daily in such amounts. In certain embodiments, the synbiotic product is administered such that the amount of prebiotic carbohydrate is from about 10 g to about 25 g carbohydrate in any single day. In certain embodiments, the synbiotic product is administered daily in such amounts. In certain embodiments, the synbiotic product is administered such that the amount of prebiotic carbohydrate is from about 10 g to about 20 g carbohydrate in any single day. In certain embodiments, the synbiotic product is administered daily in such amounts.

In certain embodiments, the synbiotic product is administered such that the amount of probiotic bacteria is from about $10^4$ CFU to about $10^{10}$ CFU in any single day. In certain embodiments, the synbiotic product is administered daily in such amounts. In certain embodiments, the synbiotic product is administered such that the amount of probiotic bacteria is from about $10^6$ CFU to about $10^8$ CFU in any single day. In certain embodiments, the synbiotic product is administered daily in such amounts. In certain embodiments, the synbiotic product is administered such that the amount of probiotic bacteria is from about $10^4$ CFU per day to about $10^6$ CFU in any single day. In certain embodiments, the synbiotic product is administered daily in such amounts. In certain embodiments, the synbiotic product is administered such that the amount of probiotic bacteria is from about $10^4$ CFU per day to about $10^8$ CFU in any single day. In certain embodiments, the synbiotic product is administered daily in such amounts. In certain embodiments, the synbiotic product is administered such that the amount of probiotic bacteria is from about $10^6$ CFU per day to about $10^{10}$ CFU in any single day. In certain embodiments, the synbiotic product is administered daily in such amounts. In certain embodiments, the synbiotic product is administered such that the amount of probiotic bacteria is from about $10^8$ CFU per day to about $10^{10}$ CFU in any single day. In certain embodiments, the synbiotic product is administered daily in such amounts.

Because it is believed that the components of the synbiotic product provide their benefit within the gastro-intestinal tract, administration of the synbiotic product may involve administration wherein the synbiotic product is exposed to the gastro-intestinal tract. In certain embodiments the synbiotic product is an ingredient or component of an edible food product such as a foodstuff or animal feed. Administration of the synbiotic product is through the consumption of a food product comprising the synbiotic product. The amount of food product comprising the synbiotic product consumed is an amount containing an effective amount of the synbiotic product.

In certain embodiments, the amount of food product consumed is an amount containing an amount of synbiotic product such that the amount of prebiotic carbohydrate is from about 1 g to about 25 g carbohydrate in any single day. In certain embodiments, the food product is consumed daily in such amounts. In certain embodiments, the amount of food product consumed is an amount containing an amount of synbiotic product such that the amount of prebiotic carbohydrate is from about 1 g to about 10 g carbohydrate in any single day. In certain embodiments, the food product is consumed daily in such amounts. In certain embodiments, the amount of food product consumed is an amount containing an amount of synbiotic product such that the amount of prebiotic carbohydrate is from about 1 g to about 20 g carbohydrate in any single day. In certain embodiments, the food product is consumed daily in such amounts. In certain embodiments, the amount of food product consumed is an amount containing an amount of synbiotic product such that the amount of prebiotic carbohydrate component is from about 2.5 g to about 10 g carbohydrate in a single day. In certain embodiments, the food product is consumed daily in such amounts. In certain embodiments, the amount of food product consumed is an amount containing an amount of synbiotic product such that the amount of prebiotic carbohydrate component is from about 2.5 g to about 20 g carbohydrate in a single day. In certain embodiments, the food product is consumed daily in such amounts. In certain embodiments, the amount of food product consumed is an amount containing an amount of synbiotic product such that the amount of prebiotic carbohydrate is from about 5 g to about 10 g carbohydrate in any single day. In certain embodiments, the food product is consumed daily in such amounts. In certain embodiments, the amount of food product consumed is an amount containing an amount of synbiotic product such that the amount of prebiotic carbohydrate is from about 5 g to about 20 g carbohydrate in any single day. In certain embodiments, the food product is consumed daily in such amounts. In certain embodiments, the amount of food product consumed is an amount containing an amount of synbiotic product such that the amount of prebiotic carbohydrate is from about 2.5 g to about 25 g carbohydrate in any single day. In certain embodiments, the food product is consumed daily in such amounts. In certain embodiments, the amount of food product consumed is an amount containing an amount of synbiotic product such that the amount of prebiotic carbohydrate component is from about 5 g to about 25 g carbohydrate in any single day. In certain embodiments, the food product is consumed daily in such amounts. In certain embodiments, the amount of food product consumed is an amount containing an amount of synbiotic product such that the amount of prebiotic carbohydrate is from about 10 g to about 25 g carbohydrate in any single day. In certain embodiments, the food product is consumed daily in such amounts. In certain embodiments, the amount of food product consumed is an amount containing an amount of synbiotic product such that the amount of prebiotic carbohydrate is from about 10 g to about 20 g carbohydrate in any single day. In certain embodiments, the food product is consumed daily in such amounts.

In certain embodiments, the amount of food product consumed is an amount containing an amount of synbiotic product such that the amount of probiotic bacteria is from about $10^4$ CFU to about $10^{10}$ CFU in any single day. In certain embodiments, the food product is consumed daily in such amounts. In certain embodiments, the amount of food product consumed is an amount containing an amount of synbiotic product such that the amount of probiotic bacteria is from about $10^6$ CFU to about $10^8$ CFU in any single day. In certain embodiments, the food product is consumed daily in such amounts. In certain embodiments, the amount of food product consumed is an amount containing an amount of synbiotic product such that the amount of probiotic bacteria is from about $10^4$ CFU to about $10^6$ CFU in any single day. In certain embodiments, the food product is consumed daily in such amounts. In certain embodiments, the amount of food product consumed is an amount containing an amount of synbiotic product such that the amount of probiotic bacteria is from about $10^4$ CFU to about $10^8$ CFU in any single day. In certain embodiments, the food product is consumed daily in such amounts. In certain embodiments, the amount of food product consumed is an amount containing an amount of synbiotic product such that the amount of probiotic bacteria is from about $10^6$ CFU to about $10^{10}$ CFU in any single day. In certain embodiments, the food product is consumed daily in such amounts. In certain embodiments, the amount of food product consumed is an amount containing an amount of synbiotic product such that the amount of probiotic bacteria is from about $10^8$ CFU to about $10^{10}$ CFU in any single day. In certain embodiments, the food product is consumed daily in such amounts.

VIII. EXAMPLES

The following disclosed embodiments are merely representative of the invention which may be embodied in various forms. Thus, specific structural, functional, and procedural details disclosed in the following examples are not to be interpreted as limiting.

Example 1

Growth of Probiotic *Bacillus* on Various Prebiotic Carbohydrates

Figure 1:
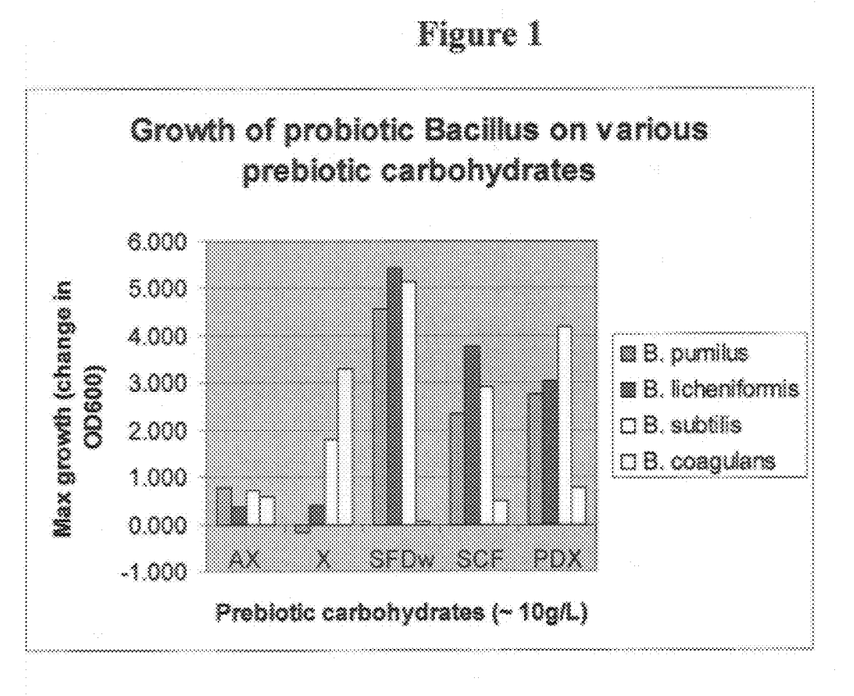
FIG. 1 shows the growth of four commercial spore forming probiotic *Bacillus* strains on prebiotic carbohydrates.

Four commercial spore-forming probiotic *Bacillus* strains were grown on prebiotic carbohydrates at 10 g/L. (See FIG. 1). The four strains were *B. pumilus*, *B. licheniformis*, *B. subtilis*, and *B. coagulans*. The prebiotic carbohydrates were high molecular weight arabinoxylan (AX), xylose (X), soluble fiber dextrin (waxy) (SFDw), soluble corn fiber (85) (SCF), and polydextrose (PDX). As a measure of the significance of the data shown in FIG. 1, Table 1 indicates P values for the *B. coagulans* data.

TABLE 1

Maximum Growth of *B. coagulans* on Various Prebiotic Substrates Relative to Maximum Growth on "None" (no added carbohydrates).

| | |
|---|---|
| Arabinoxylan (high molecular weight) (AX) | P < 0.01 |
| Xylose (X) | P < 0.01 |
| Soluble Fiber Dextrin (waxy) (SFDw) | P > 0.75 |
| Soluble Corn Fiber (85) (SCF) | P < 0.02 |
| Polydextrose (PDX) | P < 0.01 |

There was significant growth of *B. coagulans* on four of five of the prebiotic substrates. No significant growth was observed on SFDw. The significant response of *B. coagulans* to the prebiotics in this study provides a comparison for determining significant growth for other probiotic strains.

Soluble fiber dextrin (SFDw). The three commercial probiotic Bacillus strains from Envera (Coatesville, Pa.)—*B. pumilus*, *B. licheniformis*, and *B. subtilis*—grew strongly on SFDw. *B. coagulans*, however, did not grow on SFDw.

Soluble corn fiber (SCF) and polydextrose (PDX). *B. pumilus*, *B. licheniformis*, and *B. subtilis* grew moderately to strongly on SCF and PDX.

Arabinoxylan (AX). All four probiotic Bacillus strains tested—*B. pumilus*, *B. licheniformis*, *B. subtilis*, and *B. coagulans*—had limited, but significant, growth on AX. Without being limited by theory, it is believed that these strains can extract limited amounts of nutrients from AX. It has been reported that *Bacillus* strains have β-xylanase, arabinosidase, and ferulic acid esterase activities that might trim sugars and/or ferulic acid from the high molecular weight AX polymers as nutrients.

Xylose (X). *B. coagulans* and *B. subtilis* grew on xylose. *B. licheniformis* showed limited growth on xylose. *B. pumilus* did not appear able to grow on xylose.

Summary. This Example 1 illustrates that known spore-forming probiotic bacteria are capable of growth on prebiotic carbohydrates such as soluble fiber dextrin, soluble corn fiber, polydextrose, high molecular weight arabinoxylan, and xylose. Each of the probiotic *Bacillus* strains showed a somewhat different substrate preference. However, none appear limited to only a single one of the tested prebiotic candidates.

Example 2

Comparison of Maximum Growth of *B. coagulans* on Various Carbohydrates

Figure 2:
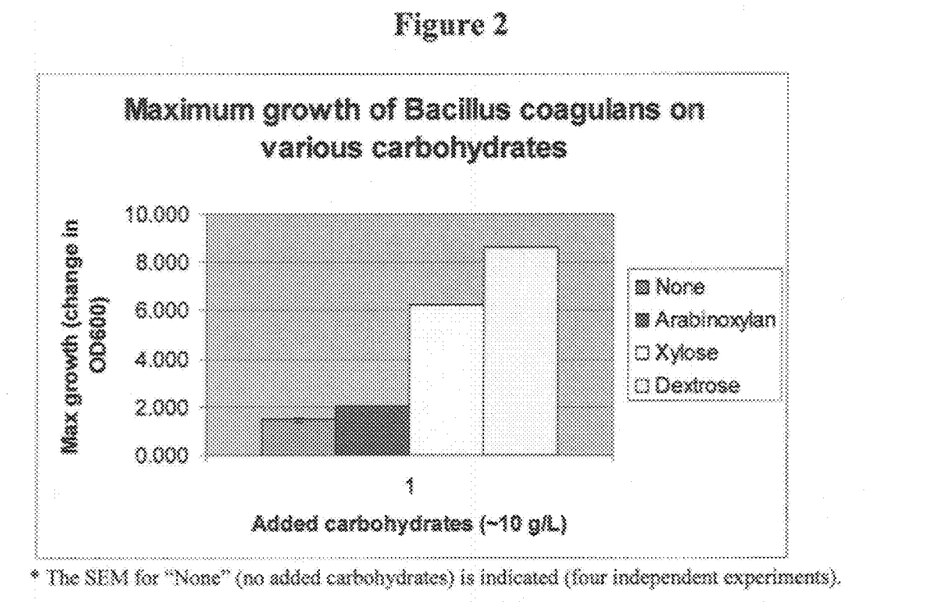
FIG. 2 shows a comparison of the maximum growth of *B. Coagulans* probiotic strain, GBI-30, on arabinoxylan, xylose, and dextrose.

The maximum growth of probiotic B. coagulans strain GBI-30 (ATCC Designation Number PTA-6086; U.S. Pat. No. 6,849,256) (Ganeden Biotech, Inc.; Mayfield Heights, Ohio) was compared on the carbohydrates arabinoxylan, xylose, and dextrose at ~10 g/L and against addition of no carbohydrates (FIG. 2). The results demonstrate that a known spore-forming probiotic bacteria is capable of strong growth on prebiotic carbohydrates such as xylose.

Example 3

Pour Plate Method for Determining the Viable Spore Count

To avoid the possibility of error, it is preferable to carry out spore counts in not less than three samples of spore concentrate because spores have a tendency to clump together and settle. Clumps should be dispersed by thorough agitation, such as shaking, before drawing samples for counting.
Protocol:
 A. Put 8 test tubes in a test rack, number them, and add 9 ml of physiological saline solution to each tube.
 B. Transfer one ml of spore suspension in the tube No. 1 by a pipette or tuberculin syringe.
 C. By using a fresh tuberculin syringe or pipette, mix the first dilution several times and transfer 1 ml into the next tube. Make the remaining tenfold dilutions in the same way using a fresh syringe or pipette for each dilution.
 D. Starting from highest dilution, pipette 1 ml from each dilution of $10^{-8}$, $10^{-7}$, and $10^{-6}$ into Petri dishes. For each dilution, five Petri dishes of 10 cm diameter are used.
 E. Pour into each Petri dish about 20 ml of melted nutrient agar cooled to 45° C. Mix the inoculum immediately with the agar by rotating the plates. Keep the plates at room temperature to allow the agar to set.
 F. Incubate the plates at 37° C. for 24 hours.
 G. Count the colonies in all five plates of a particular dilution. Multiply the average number per plate by the dilution factor to obtain the viable count per ml in original suspension. Calculate the average count for each dilution from $10^{-6}$ to $10^{-8}$. To obtain the average viable count in original stock suspension, take the average of three dilutions.

Example 4

Supplement

Start with a suspension of *Bacillus coagulans* (BC) freeze-dried spore powder which contains at least $10^9$ viable spores per gram powder. Xylose powder (X), can be obtained from Sigma-Aldrich (St. Louis, Mo., USA). The two powders are mixed in an X/BC ratio of 100/1 until a homogeneous product is obtained. Sachets are filled with 2-5 g of this mixture, depending on the dosage regime (e.g., 5 g for one sachet per day or 3 g for two sachets per day). The contents of one sachet can, for example, be taken mixed in a glass of orange juice or milk.

Example 5

Synbiotic Nutritional Bar

A 23 g bar is prepared from 4.0 g oat flakes, 4.0 g wheat flakes, 3.0 g puffed rice, 1.0 g crushed hazelnuts, 0.25 g honey, 3.0 g raisins, 1.5 g maltodextrin, 1.0 g freeze-dried *Bacillus coagulans* (BC; $>10^9$ viable spores per gram powder), and 5.0 g Xylose powder.

Example 6

Synbiotic Mixture for Mixing with a Complete Enteral Clinical Nutrition

A synbiotic product, powder mixture is prepared in accordance with the method of Example 4. 5 g of the powder mixture is placed in a sachet. The contents of this sachet can be added to a standard enteral clinical nutrition. For best results, it is preferable that the contents of the sachet are added not more than 30 minutes before use.

Example 7

Synbiotic Powder Mixture for Fortifying Baby Food

A synbiotic product, powder mixture is prepared in accordance with the method of Example 4. 5 g of the powder mixture is placed in a sachet. The contents of this sachet can be added to a standard baby formula or baby food. For best results, it is preferable that the contents of the sachet are added not more than 30 minutes before use.

Example 8

Sweet Powder Coating for Dry Food Stuffs

A sweet powder coating may be prepared, such as for a powdered coating for dry foodstuffs including bakery goods, etc.

Another example is a chewing gum with a dry powdered coating of the synbiotic mixture that is prepared with the synbiotic product, powder mixture prepared in accordance with Example 4. The mildly sweet, non-cariogenic powder is used to coat sticks of chewing gum. The sticks of chewing gum may be packaged using standard packaging methods as individually wrapped gum sticks.

What is claimed is:

1. A synbiotic product comprising soluble corn fiber, and at least one probiotic spore-forming *Bacillus* bacteria selected from the group consisting of *B. subtilis, B. licheniformis, B. pumilis,* and mixtures thereof.

2. The synbiotic product of claim 1 wherein the spore-forming *Bacillus* bacteria is *B. licheniformis.*

3. A food product comprising a synbiotic product of claim 1.

4. A method of increasing the titer of a spore-forming *Bacillus* bacteria in the intestinal tract of a mammal, the method comprising administering to the mammal an effective amount of the synbiotic product of claim 1.

5. The method of claim 4 wherein the synbiotic product is administered such that the amount of prebiotic carbohydrate is from about 1 g to about 25 g in any one day and the amount of probiotic spore-forming *Bacillus* bacteria is from about $10^4$ CFU to about $10^{10}$ CFU in any one day.

6. The method of claim 5 wherein the synbiotic product is administered such that the amount of prebiotic carbohydrate is from about 2.5 g to about 10 g in any one day and the amount of probiotic spore-forming *Bacillus* bacteria is from about $10^6$ CFU to about $10^8$ CFU in any one day.

7. The method of claim 4 wherein the synbiotic product is administered daily.

8. The method of claim 4 wherein the synbiotic product is administered through the consumption of a food product comprising the synbiotic product.

9. The method of claim 8 wherein the food product consumed is a foodstuff and the mammal is a human.

10. The method of claim 8 wherein the food product consumed is an animal feed and the mammal is a non-human mammal.

11. The method of claim 10 wherein the mammal is selected from the group comprising horses, cattle, swine, sheep, goats, oxen, llamas, alpacas, and bison.

12. The method of claim 10 wherein the mammal is a cat or dog.

13. The method of claim 10 wherein antibiotics are not administered to the non-human mammal.

14. A synbiotic product comprising a prebiotic carbohydrate component and a probiotic spore component, wherein the prebiotic carbohydrate component comprises at soluble corn fiber and the probiotic spore component comprises at least one probiotic spore-forming *Bacillus* bacteria selected from the group consisting of *B. subtilis, B. licheniformis, B. pumilis*, and mixtures thereof.

15. The synbiotic product of claim 14 wherein the spore-forming *Bacillus* bacteria is *B. licheniformis*.

16. The synbiotic product of claim 14 wherein the probiotic spore component comprises up to about $10^{11}$ viable spores per gram dry weight.

17. The synbiotic product of claim 14 wherein the probiotic spore component comprises from about $10^9$ to about $10^{11}$ viable spores per gram dry weight.

18. The synbiotic product of claim 14 wherein the synbiotic product comprises at least about $10^5$ viable probiotic spores per gram dry weight.

19. The synbiotic product of claim 14 wherein the synbiotic product comprises from about $10^5$ to about $10^7$ viable probiotic spores per gram dry weight.

20. A food product comprising a synbiotic product of claim 14.

21. A method of increasing the titer of a spore-forming *Bacillus* bacteria in the intestinal tract of a mammal, the method comprising administering to the mammal an effective amount of the synbiotic product of claim 14.

22. The method of claim 21 wherein the synbiotic product is administered such that the amount of prebiotic carbohydrate is from about 1 g to about 25 g in any one day and the amount of probiotic spore-forming *Bacillus* bacteria is from about $10^4$ CFU to about $10^{10}$ CFU in any one day.

23. The method of claim 22 wherein the synbiotic product is administered such that the amount of prebiotic carbohydrate is from about 2.5 g to about 10 g in any one day and the amount of probiotic spore-forming *Bacillus* bacteria is from about $10^6$ CFU to about $10^8$ CFU in any one day.

24. The method of claim 21 wherein the synbiotic product is administered daily.

25. The method of claim 21 wherein the synbiotic product is administered through the consumption of a food product comprising the synbiotic product.

26. The method of claim 25 wherein the food product consumed is a foodstuff and the mammal is a human.

27. The method of claim 25 wherein the food product consumed is an animal feed and the mammal is a non-human mammal.

28. The method of claim 27 wherein the mammal is selected from the group comprising horses, cattle, swine, sheep, goats, oxen, llamas, alpacas, and bison.

29. The method of claim 27 wherein the mammal is a cat or dog.

30. The method of claim 27 wherein antibiotics are not administered to the non-human mammal.

* * * * *